US011937978B2

(12) United States Patent
Yeom et al.

(10) Patent No.: US 11,937,978 B2
(45) Date of Patent: Mar. 26, 2024

(54) HANDHELD ULTRASOUND AND NUCLEAR MEDICINE FUSION IMAGING DEVICE

(71) Applicant: Korea University Research and Business Foundation, Seoul (KR)

(72) Inventors: Jung Yeol Yeom, Seoul (KR); Muhammad Nasir Ullah, Gumi-si (KR); Chan Ho Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 229 days.

(21) Appl. No.: 17/191,815

(22) Filed: Mar. 4, 2021

(65) Prior Publication Data
US 2021/0186465 A1 Jun. 24, 2021

Related U.S. Application Data

(63) Continuation of application No. PCT/KR2020/008743, filed on Jul. 3, 2020.

(30) Foreign Application Priority Data

Jul. 5, 2019 (KR) .................. 10-2019-0081270
Jun. 19, 2020 (KR) .................. 10-2020-0075014

(51) Int. Cl.
*A61B 8/00* (2006.01)
*A61B 6/00* (2006.01)
(Continued)

(52) U.S. Cl.
CPC .......... *A61B 8/4444* (2013.01); *A61B 6/4258* (2013.01); *A61B 6/4417* (2013.01);
(Continued)

(58) Field of Classification Search
CPC ... A61B 8/4444; A61B 6/4258; A61B 6/4417; A61B 8/4416; A61B 6/4405; A61B 8/4483; G01T 1/20; G01T 1/24
See application file for complete search history.

(56) References Cited

U.S. PATENT DOCUMENTS 4,221,132 A    9/1980 Poole
4,995,396 A  *  2/1991 Inaba ................. G01T 1/161
                                                    600/463
(Continued)

FOREIGN PATENT DOCUMENTS

CN    102113892 A    7/2011
CN    104688267 A    6/2015
(Continued)

OTHER PUBLICATIONS

Samira Abbaspour et al., Cadmium Telluride Semiconductor Detector for Improved Spatial and Energy Resolution Radioisotopic Imaging, (2017), World Journal of Nuclear Medicine (Year: 2017).*
(Continued)

*Primary Examiner* — Joel Lamprecht
*Assistant Examiner* — Brooke Lyn Klein
(74) *Attorney, Agent, or Firm* — NSIP Law (57) ABSTRACT

The present disclosure provides a new concept of fusion imaging device for simultaneously providing anatomical information and functional/biochemical information of human bodies, to accurately localize lesions in the preoperative process and measure in real time, thereby ensuring the stability of patients with lower radiation doses than the existing fusion imaging devices such as positron emission tomography (PET)/computed tomography (CT) and single photon emission computed tomography (SPECT)/CT, and includes: a transducer to transmit and receive an ultrasound; a matching layer positioned on top of the transducer to reduce a difference in acoustic resistance between the trans- (Continued)

ducer and an affected part, to support an ultrasound beam to be smoothly transmitted into tissues and a reflected beam to be received with high sensitivity; a backing member to absorb the ultrasound on an opposite side of the affected part with respect to the transducer; and a scintillator to detect gamma rays which are radiation, wherein an ultrasound medical device and a nuclear medicine detector are combined into one probe using the backing member as a collimator of a nuclear medicine probe.

2 Claims, 10 Drawing Sheets
(10 of 10 Drawing Sheet(s) Filed in Color)

(51) Int. Cl.
*G01T 1/20* (2006.01)
*G01T 1/24* (2006.01)

(52) U.S. Cl.
CPC .............. *A61B 8/4416* (2013.01); *G01T 1/20* (2013.01); *A61B 6/4405* (2013.01); *A61B 8/4483* (2013.01); *G01T 1/24* (2013.01)

(56) References Cited

U.S. PATENT DOCUMENTS

| | | | |
|---|---|---|---|
| 2007/0051892 | A1 | 3/2007 | Warburton et al. |
| 2008/0208044 | A1 | 8/2008 | Lecoq et al. |
| 2014/0276032 | A1* | 9/2014 | Majewski ............ A61B 8/4254 600/431 |
| 2015/0157292 | A1* | 6/2015 | Gu ........................ A61B 8/4488 600/459 |
| 2017/0079609 | A1* | 3/2017 | Pani ........................ A61B 8/463 |

FOREIGN PATENT DOCUMENTS

| | | |
|---|---|---|
| CN | 104703548 A | 6/2015 |
| CN | 105708499 A | 6/2016 |
| CN | 107567315 A | 1/2018 |
| CN | 109069086 A | 12/2018 |
| JP | 6-205757 A | 7/1994 |
| KR | 10-2012-0000722 A | 1/2012 |
| KR | 10-2012-0091737 A | 8/2012 |
| KR | 10-1496275 B1 | 2/2015 |
| KR | 10-1646700 B1 | 8/2016 |
| KR | 10-1670335 B1 | 10/2016 |

OTHER PUBLICATIONS

International Search Report dated Oct. 29, 2020 in counterpart International Patent Application No. PCT/KR2020/008743 (3 pages in English and 2 pages in Korean).

International Search Report dated Oct. 10, 2022, in counterpart International Patent Application No. PCT/KR2020/008743 (3 Pages in Korean).

Chinese Office Action dated Nov. 9, 2023 in corresponding Chinese Patent Application No. 202080004942.0 (8 pages in Chinese).

* cited by examiner

HANDHELD ULTRASOUND AND NUCLEAR MEDICINE FUSION IMAGING DEVICE

CROSS REFERENCE TO RELATED APPLICATIONS

Pursuant to 35 U.S.C. §§ 120 and 365(c), this application is a Bypass Continuation of International Application No. PCT/KR2020/008743, filed on Jul. 3, 2020, which claims the benefit under 35 U.S.C. §§ 119(a) and 365(b) of Korean Patent Application No. 10-2019-0081270, filed on Jul. 5, 2019, and Korean Patent Application No. 10-2020-0075014, filed on Jun. 19, 2020 in the Korean Intellectual Property Office, the entire disclosure of which is incorporated herein by reference for all purposes.

TECHNICAL FIELD

The present disclosure relates to a handheld ultrasound-nuclear medicine fusion imaging device for precise cancer diagnosis and surgery, and more particularly, to a new concept of fusion imaging device for simultaneously providing anatomical information and functional/biochemical information of human bodies, thereby accurately localizing lesions in the pre-operative process and measuring in real time.

BACKGROUND ART

The population is ageing fast, and the cancer incidence rate is also increasing rapidly every year. With the growing social attention to quality of life and health, there is an increasing demand for medical services of high level such as precision surgery.

Nuclear medicine imaging devices using radioactive isotope such as gamma cameras, positron emission tomography (PET) and single photon emission computed tomography (SPECT) can image functional and biochemical information of living bodies, so they are usefully used to define pathological phenomena, diagnose diseases, determine prognosis after treatment and plan treatment. However, nuclear medicine imaging which provides molecular imaging lacks anatomical information provided in terms of the biochemical principles and the physical principles, and it is difficult to accurately localize diseases due to the low resolution and costs so much.

On the other hand, equipment for anatomical imaging such as magnetic resonance imaging (MRI), ultrasound (US) and computed tomography (CT) provides high image resolution, but is difficult to provide functional/biochemical information of living bodies.

Figure 1:
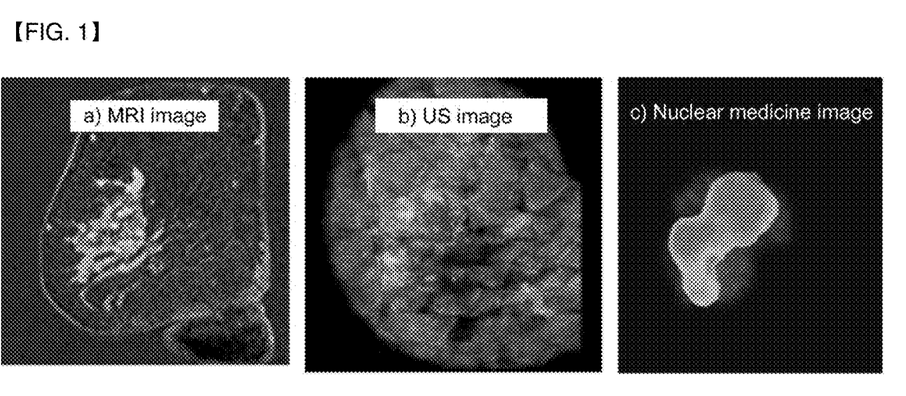
FIG. 1 shows an example of an MRI image (a), an ultrasound image (b) and a nuclear medicine image (c) of a breast cancer patient.

Accordingly, there is a need for fusion imaging devices that can overcome the disadvantages of nuclear medicine imaging by adding anatomical information that can be acquired from MRI, X-rays, CT or ultrasound to function information unique to nuclear medicine imaging. Referring to FIG. 1, shown is an example of an MRI image (a), an ultrasound image (b) a nuclear medicine imaging (c) of a breast cancer patient, and a breast cancer unseen in the ultrasound image is clearly seen in the nuclear medicine image.

Currently, the most widely used fusion imaging device, PET/CT, has diagnostic advantages since it is possible to accurately identify the location and size of lesions by fusion of PET images having low spatial resolution and less anatomical information and CT images having high spatial resolution but no functional and biochemical information of living bodies.

159 PETs and PET/CTs, to be exact, 11 PETs and 148 PET/CTs are installed in domestic areas (as of 2015), and recently, with the growing attention to fusion imaging devices such as PET/MRI and PET/optical, studies on new fusion imaging devices are increasingly conducted. However, the most widely used PET/CT so far cannot be used in real time and thus it is impossible to use PET/CT during surgery and there is a risk that patients may be exposed to very high levels of radiation.

Accordingly, there is a need to develop a new concept of fusion imaging device that can be used in real time and minimizes the radiation exposure to human bodies. Meanwhile, in the field of nuclear medicine, as opposed to PET and SPECT, gamma detectors and gamma cameras can be made in the form of handheld probes and they are often used for early diagnosis of diseases such as cancers, detection or monitoring of cancers during surgery and lymph node biopsy (determining whether there is a metastatic cancer).

Because of ultrasound that is not harmful to human bodies, no need for pretreatment including contrast medium injection and high accuracy, ultrasonic medical devices are often used to diagnose human organs.

DISCLOSURE

Technical Problem

To solve the above-described problem, the present disclosure is directed to providing a new concept of fusion imaging device for simultaneously providing anatomical information and functional/biochemical information of human bodies, to accurately localize lesions in the pre-operative process and measure in real time, thereby ensuring the stability of patients with lower radiation doses than the existing fusion imaging devices such as positron emission tomography (PET)/computed tomography (CT) and single photon emission computed tomography (SPECT)/CT.

In addition, the present disclosure is aimed at improving the accuracy and stability of cancer tissue necrosis in a noninvasive manner through combination with the high intensity focused ultrasound (HIFU) therapeutic technique.

Technical Solution

To achieve the above-described object, a handheld ultrasound and nuclear medicine fusion imaging device according to the present disclosure includes: a transducer to transmit and receive an ultrasound; a matching layer positioned on top of the transducer to reduce a difference in acoustic resistance between the transducer and an affected part, to support an ultrasound beam to be smoothly transmitted into tissues and a reflected beam to be received with high sensitivity; a backing member to absorb the ultrasound on an opposite side of the affected part with respect to the transducer; and a scintillator to detect gamma rays which are radiation, wherein an ultrasound medical device and a nuclear medicine detector are combined into one probe using the backing member as a collimator of a nuclear medicine probe.

Advantageous Effects

The present disclosure achieves more accurate diagnosis by simultaneously acquiring anatomical information and functional/biochemical information of lesions in real time in the pre-operative process using the ultrasound-nuclear medicine fusion imaging device for precise cancer diagnosis and surgery.

Additionally, it is possible to ensure the safety of patients through the exposure to less radiation than the existing fusion imaging devices such as positron emission tomography (PET)/computed tomography (CT) and single photon emission computed tomography (SPECT)/CT.

Additionally, it is possible to improve the accuracy and ensure the stability of noninvasive lesion treatment and tumor removal technology through combination with the high intensity focused ultrasound (HIFU) therapeutic technique. With the new concept of fusion imaging device that has never been seen before as described above, it is possible to expand into the development of new diagnosis and treatment methodology and pioneer new medical device markets.

The present disclosure may acquire both ultrasound signals and gamma signals through only one handheld probe, and process both ultrasound signals and gamma signals through only one circuit, thereby acquiring fusion images in real time and reducing the fabrication costs.

Additionally, it is expected to have applications in the medical field as well as in the field of nondestructive testing used to measure the thickness/density of concrete and pipes.

DESCRIPTION OF DRAWINGS

The patent or application file contains a least one drawing executed in color. Copies of this patent or patent application publication with color drawing(s) will be provided by the Office upon request and payment of the necessary fee.

BEST MODE

Hereinafter, the present disclosure will be described in more detail through embodiments. These embodiments are provided by way of illustration and it will be obvious to those skilled in the art that the scope of the present disclosure is not interpreted as being limited to the embodiments.

Hereinafter, the elements of a handheld ultrasound-nuclear medicine fusion imaging device for precise cancer diagnosis and surgery according to the present disclosure will be described.

An embodiment of an ultrasound-nuclear medicine fusion probe has a nuclear medicine collimator design method using an ultrasound backing material.

A transducer of an ultrasound medical device mainly uses PZT, PMN, LTGA, LNGA crystals as a device for transmitting/receiving an ultrasound. The transducer is a device which produces an ultrasound when receiving an electric current, and produces an electric current when receiving an ultrasound. As the direction of the produced ultrasound is radial, the image quality of an affected part which is a region of interest may deteriorate due to the ultrasound produced on the opposite side of the affected part.

To prevent this problem, a backing material (epoxy+ tungsten powder) for absorbing the ultrasound is disposed on the opposite side of the affected part with respect to the transducer to attenuate the ultrasound of the opposite direction causing the image quality deterioration. In general, the backing material is made of a high density material to attenuate the ultrasound.

On the other hand, in the case of gamma rays, due to its high transmittance, to accurately detect a desired location, a collimator is necessary to limit the direction of gamma rays. The collimator is also made of a high density material to attenuate gamma rays coming from an unwanted direction.

Figure 2:
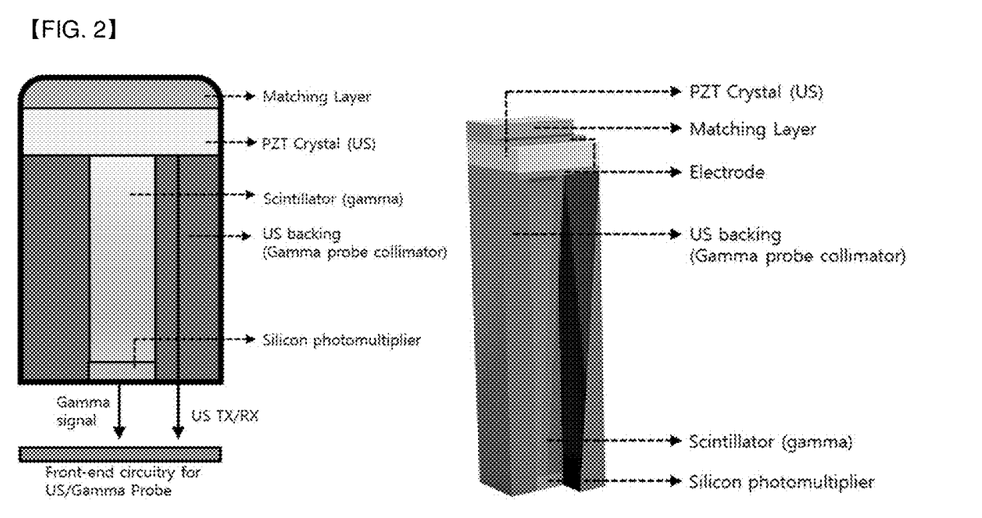
FIG. 2 is a diagram showing the structure of an ultrasound-nuclear medicine fusion diagnostic probe using a scintillator and a photosensor according to an embodiment of the present disclosure.

Accordingly, as shown in FIG. 2, an ultrasound medical device and a nuclear medicine detector are combined into one probe through a new idea of using a backing material of an ultrasound medical device as a collimator. In FIG. 2, a matching layer plays a role in reducing a difference in acoustic resistance between the probe and the skin for an ultrasound beam to be efficiently transmitted into tissues and for the reflected beam to be received with high sensitivity.

An electrode serves to transmit the electric current necessary when transmitting the ultrasound to the transducer or transmit the electric current produced when receiving the ultrasound to a circuit. A scintillator is a device which produces an amount of light that is proportional to the energy of gamma rays when receiving the gamma rays, and the produced light is transmitted to a photosensor (Silicon photomultiplier SiPM, avalanche photodiode APD), converted to an electrical signal and transmitted to the circuit.

Figure 7:
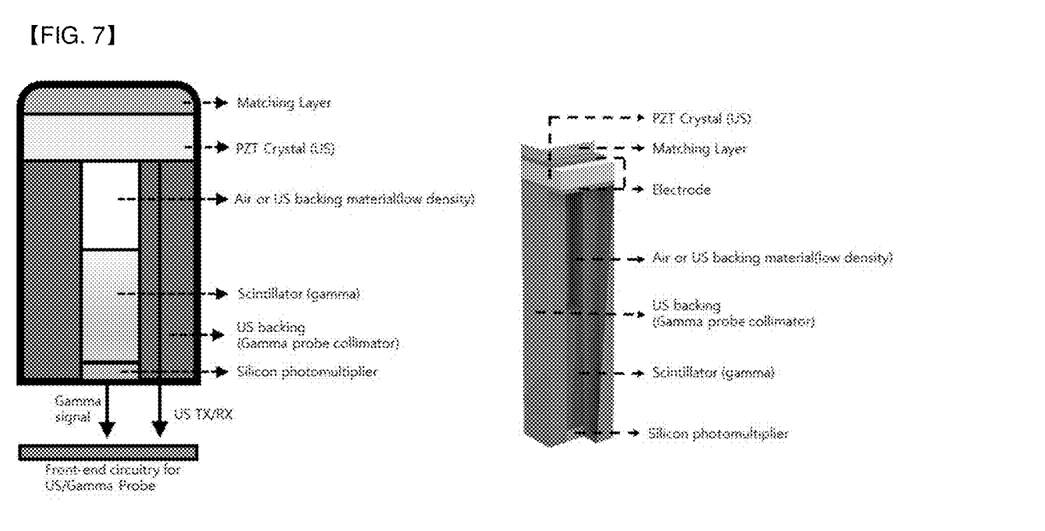
FIG. 7 is a diagram showing the structure of an ultrasound-nuclear medicine fusion diagnostic probe using a scintillator and a photosensor according to yet another embodiment of the present disclosure.

Meanwhile, as shown in FIG. 7, air or a backing material having low density may be additionally positioned between the scintillator and the electrode.

Another embodiment of the ultrasound-nuclear medicine fusion probe has a high density room temperature semiconductor radiation detector method.

Figure 3:
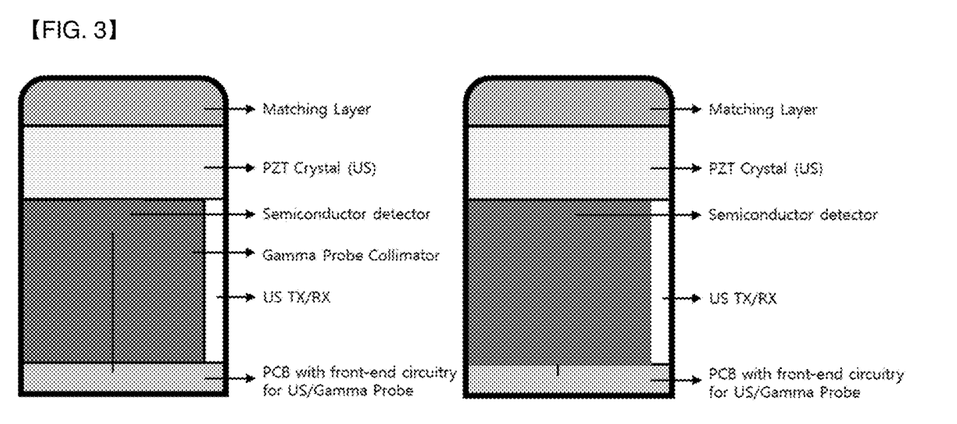
FIG. 3 is a diagram showing the structure of an ultrasound-nuclear medicine fusion diagnostic probe using a room temperature semiconductor detector according to another embodiment of the present disclosure.

Instead of the scintillator and the photosensor (SiPM, APD), the room temperature semiconductor radiation detector (for example, CZT, CdTe) is used. Due to its high density, the semiconductor radiation detector is expected to serve as a radiation detector and a backing material at the same time. Accordingly, using this, as shown in FIG. 3, the ultrasound-nuclear medicine fusion probe may be configured by replacing all or part of the backing material with the semiconductor detector.

Figure 8:
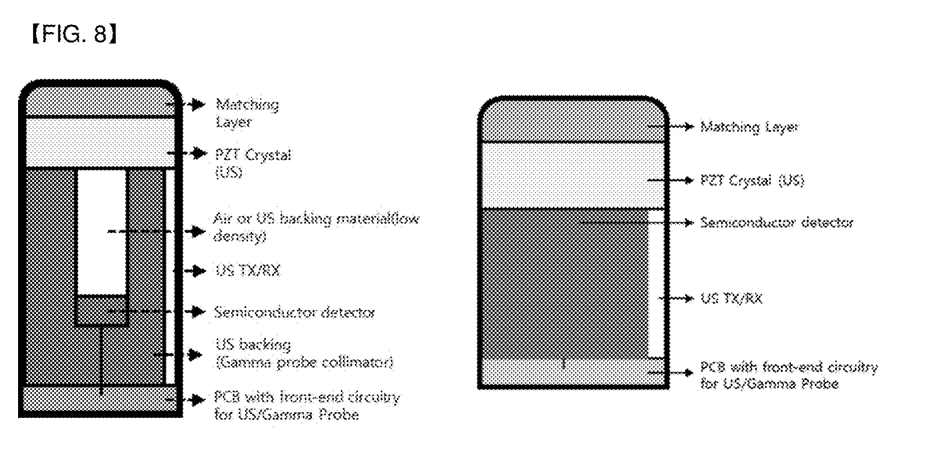
FIG. 8 is a diagram showing the structure of an ultrasound-nuclear medicine fusion diagnostic probe using a room temperature semiconductor detector according to further another embodiment of the present disclosure.

Meanwhile, as shown in FIG. 8, air or a backing material having low density may be additionally positioned between the bottom of the crystal and the semiconductor detector.

The present disclosure uses a material capable of serving as a transducer and a radiation detector at the same time.

Crystal materials such as LTGA, LNGA and SNGS may serve as a transducer which generates an electrical signal when receiving an ultrasound and produces an ultrasound when receiving an electrical signal, and at the same time, a scintillator which converts the energy of radiation to light when radiation such as gamma rays is incident. Accordingly, these materials may make it possible to detect both an ultrasound signal and a radiation signal using one detector.

Additionally, to detect light produced when radiation is incident, it is necessary to attach the photosensor to the bottom of the crystal, and to transmit/receive an ultrasound, it is necessary to attach the electrode to the top and bottom of the crystal.

Figure 4:
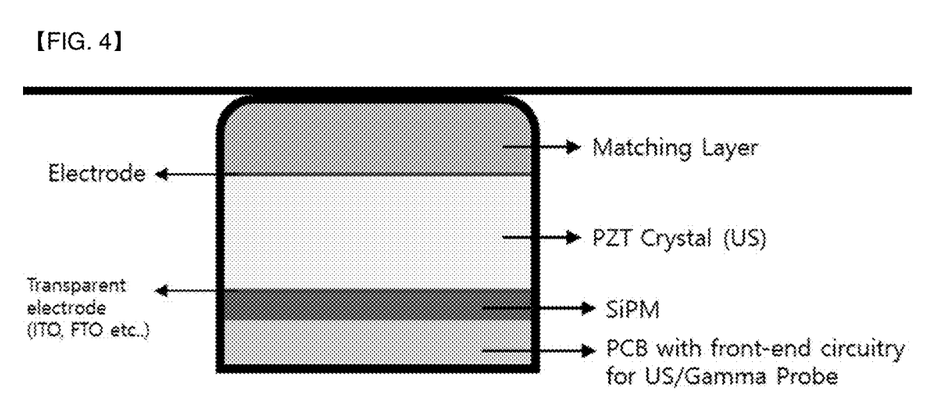
FIG. 4 shows the structure of an ultrasound-nuclear medicine fusion diagnostic probe using a material (for example, LTGA, LNGA) capable of serving as a transducer and a radiation detector at the same time according to still another embodiment of the present disclosure.

Accordingly, as shown in FIG. 4, when a transparent electrode is attached to the bottom of the crystal, the above-described requirements may be simultaneously satisfied.

The handheld ultrasound-nuclear medicine fusion imaging device according to the present disclosure has, for example, an electronic circuit method for an ultrasound/gamma fusion probe.

The ultrasound/gamma switching circuit is an integrated electronic circuit for an ultrasound-nuclear medicine fusion diagnostic probe, characterized in selectively receiving an ultrasound signal or a gamma signal using the switching circuit.

The key of the ultrasound/gamma switching circuit is to receive a gamma signal using an idle time during transmission/reception of an ultrasound signal.

Figure 5:
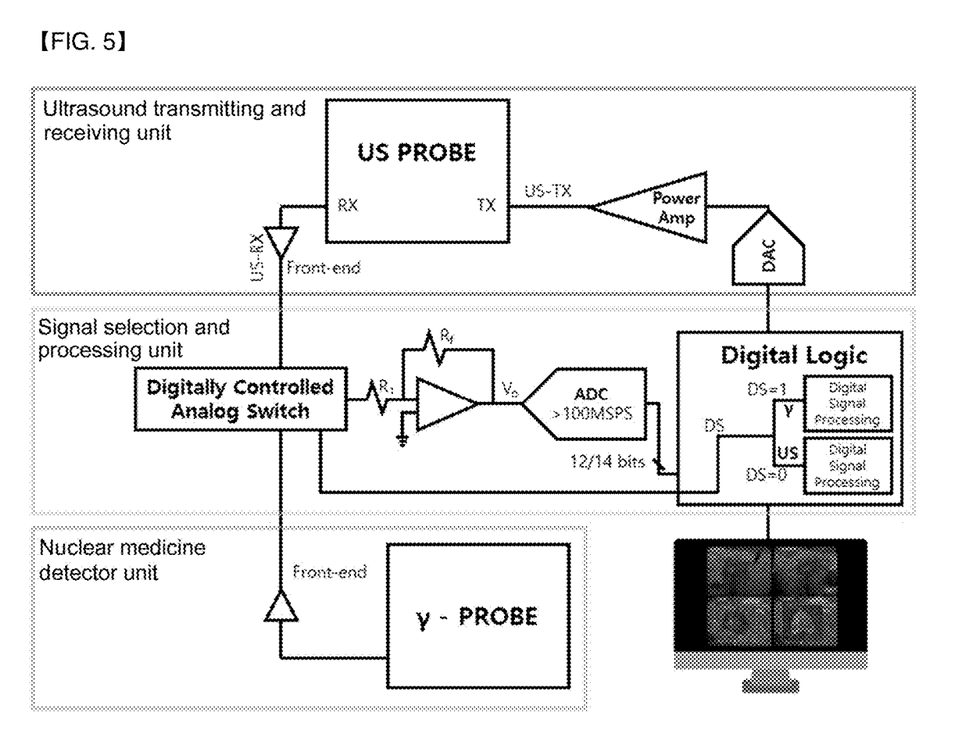
FIG. 5 shows an integrated electronic circuit for an ultrasound-nuclear medicine fusion diagnostic probe, configured to selectively receive an ultrasound signal or a gamma signal using a switching circuit.

As shown in FIG. 5, it includes an ultrasound transmitting and receiving unit, a signal selection and processing unit and a nuclear medicine detector unit, and processes an ultrasound signal and a gamma signal in an alternating manner using a digitally controlled analog switch.

Another example of the handheld ultrasound-nuclear medicine fusion imaging device according to the present disclosure has an ultrasound/gamma circuit method using a filter.

The ultrasound/gamma circuit using a filter is an integrated electronic circuit for an ultrasound-nuclear medicine fusion diagnostic probe, characterized in extracting and distinguishing an ultrasound signal and a gamma signal from a combined ultrasound/gamma signal using the filter.

Figure 6:
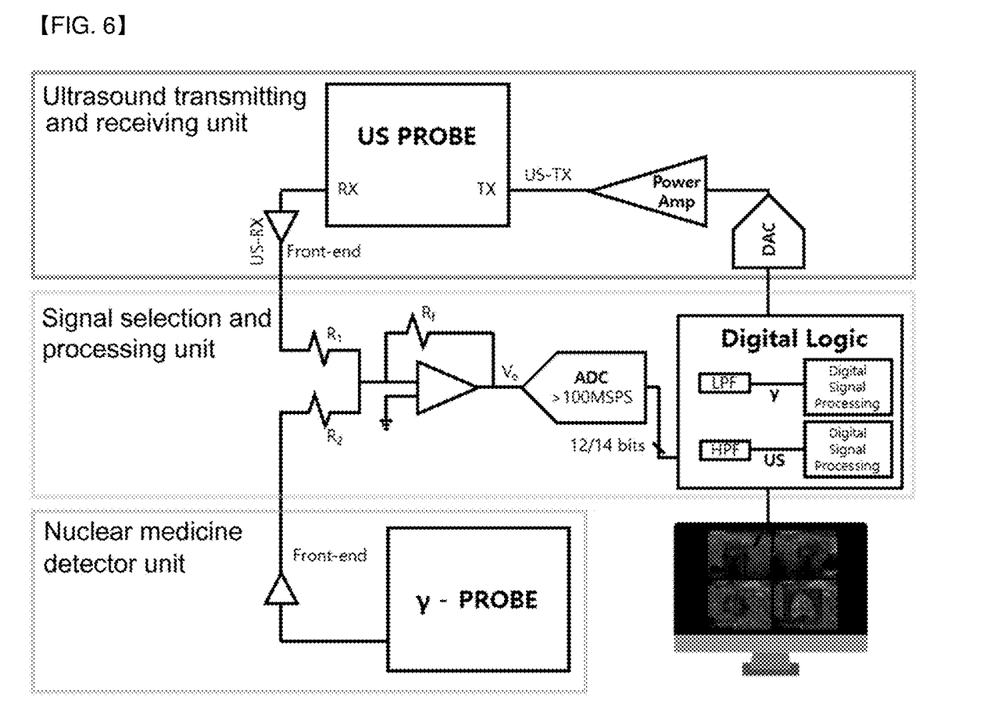
FIG. 6 shows an integrated electronic circuit for an ultrasound-nuclear medicine fusion diagnostic probe, configured to extract and distinguish an ultrasound signal and a gamma signal from a combined ultrasound/gamma signal using a filter.

The ultrasound/gamma circuit using a filter is a circuit which simultaneously receives an ultrasound signal and a gamma signal, and extracts and distinguishes the ultrasound signal and the gamma signal from a combined ultrasound/gamma signal using the filter. As shown in FIG. 6, it includes an ultrasound transmitting and receiving unit, a signal selection and processing unit and a nuclear medicine detector unit, and converts a combined signal to a digital signal through an analog-to-digital converter (ADC) and extracts and distinguishes an ultrasound signal and a gamma signal through a digital filter.

According to another embodiment of the present disclosure, an ultrasound-nuclear medicine fusion diagnostic imaging device may include an array of ultrasound-nuclear medicine fusion probes.

Figure 9:
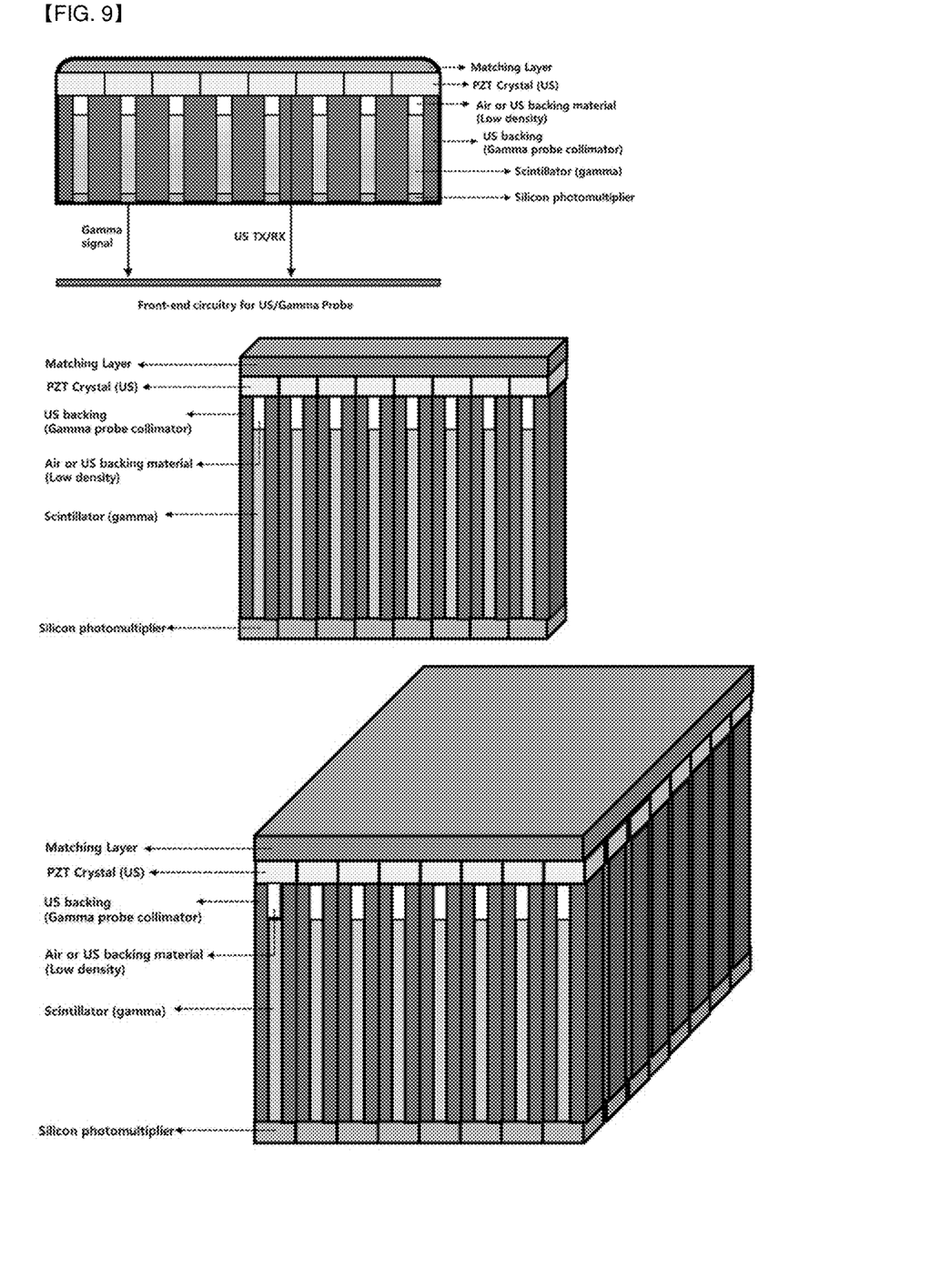
FIG. 9 is a diagram showing the structure of an ultrasound-nuclear medicine fusion diagnostic imaging device including an array of ultrasound-nuclear medicine fusion diagnostic probes using scintillators and photosensors according to even still another embodiment of the present disclosure.

In an example, as shown in FIG. 9, the ultrasound-nuclear medicine fusion diagnostic imaging device may include an array of probes connected in parallel, each probe (i.e., the probe of FIG. 7) including the transducer, the air or backing material having low density, the scintillator and the photosensor (the silicon photomultiplier).

Figure 10:
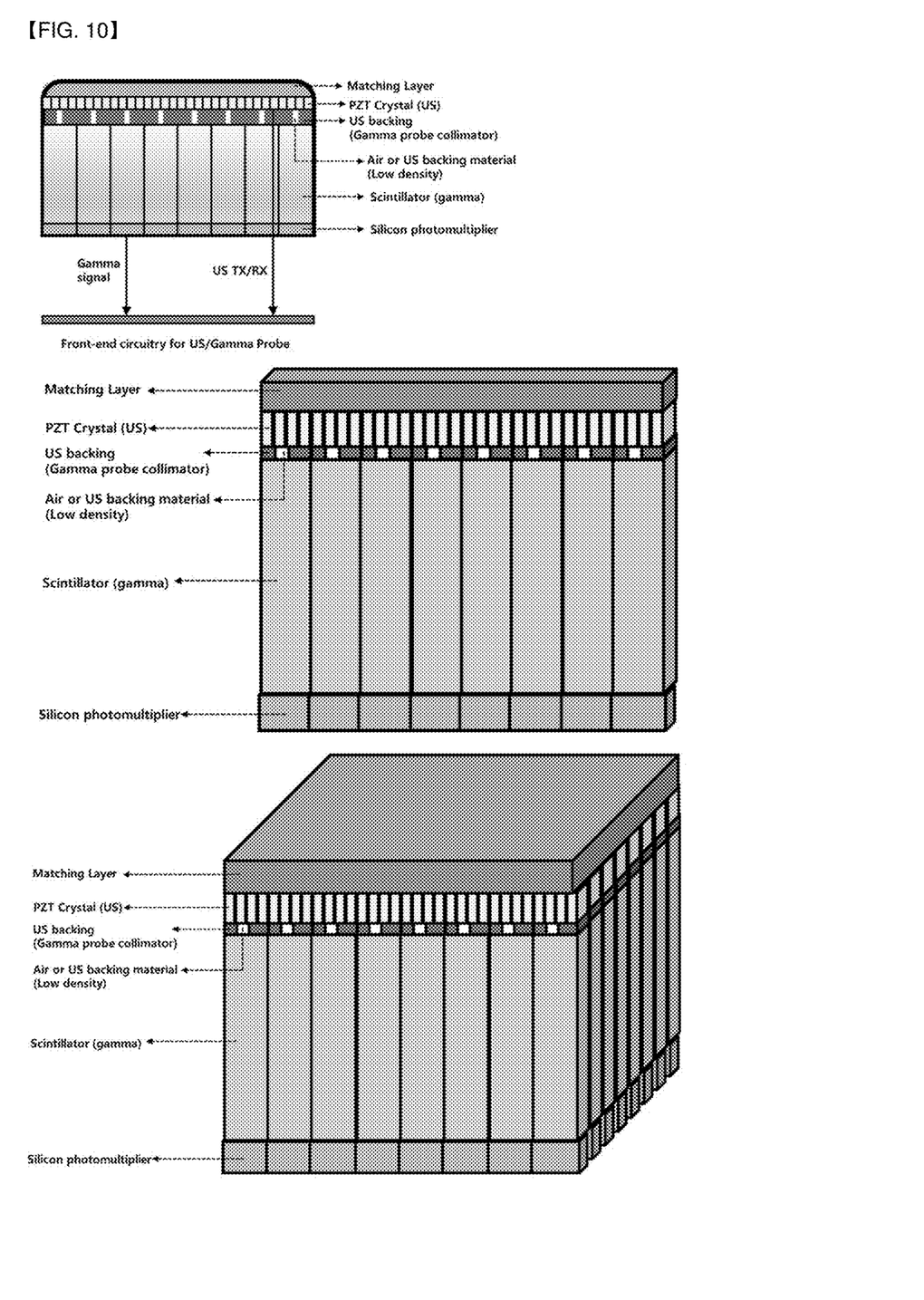
FIG. 10 is a diagram showing the structure of an ultrasound-nuclear medicine fusion diagnostic imaging device including an array of ultrasound-nuclear medicine fusion diagnostic probes using scintillators and photosensors according to even yet another embodiment of the present disclosure.

In another example, in addition to the array of probes connected in parallel as shown in FIG. 9, the transducer may include an array of small size piezoelectric elements as shown in FIG. 10 to acquire an image with higher performance. That is, the ultrasound-nuclear medicine fusion diagnostic imaging device may include the matching layer, the transducer including the array of piezoelectric elements, the US backing material (replaceable partially by air), the scintillator and the photosensor (the silicon photomultiplier) in a sequential order from the top near the skin.

While the present disclosure has been hereinabove described through the embodiments, the present disclosure is not limited thereto. Modifications and changes may be made to the embodiments without departing from the spirit and scope of the present disclosure, and those skilled in the art will understand that such modifications and changes fall in the scope of the present disclosure.

The invention claimed is:

1. A handheld ultrasound and nuclear medicine fusion imaging device, comprising:
   a transducer to transmit an ultrasound beam and receive a reflected beam;
   a matching layer disposed on a first surface of the transducer to reduce a difference in acoustic resistance between the transducer and an affected part, to support the ultrasound beam to be transmitted into tissues and the reflected beam to be received;
   an absorber comprising a first backing material disposed on a second surface of the transducer opposite to the first surface;
   wherein the first backing material comprises epoxy and tungsten
   a transmission layer disposed on the second surface comprising air or a second backing material having a lower density than the first backing material to transmit the gamma rays; and
   a scintillator disposed on the transmission layer to detect gamma rays which are generated in the affected part and transmitted through the transducer and the matching layer,
   wherein a lateral surface of the scintillator and the transmission layer are surrounded by the absorber, and
   wherein the absorber serves as an acoustic absorber and as a collimator of the handheld ultrasound and nuclear medicine fusion imaging device, thereby absorbing the ultrasound beam transmitted in a direction from the first surface to the second surface and attenuating the gamma rays coming from an unwanted direction.

2. The handheld ultrasound and nuclear medicine fusion imaging device according to claim 1, wherein the transducer comprises an array of piezoelectric elements.

\* \* \* \* \*